(12) United States Patent
Götzinger et al.

(10) Patent No.: US 7,855,839 B2
(45) Date of Patent: Dec. 21, 2010

(54) ARTIFICIAL EYE AND MEASURING INSTRUMENT FOR MEASURING THE ACCOMMODATION OF AN EYE

(75) Inventors: Volker Götzinger, Heroldsberg (DE); Andreas Schnalke, Nuremberg (DE); Arthur Michling, Fürth (DE); Kurt Heiberger, Nuremberg (DE)

(73) Assignee: Wavelight AG, Erlangen (DE)

( * ) Notice: Subject to any disclaimer, the term of this patent is extended or adjusted under 35 U.S.C. 154(b) by 12 days.

(21) Appl. No.: 11/994,060

(22) PCT Filed: Jun. 22, 2006

(86) PCT No.: PCT/EP2006/006028

§ 371 (c)(1),
(2), (4) Date: Oct. 28, 2008

(87) PCT Pub. No.: WO2007/000280

PCT Pub. Date: Jan. 4, 2007

(65) Prior Publication Data

US 2009/0128777 A1      May 21, 2009

(30) Foreign Application Priority Data

Jun. 29, 2005    (EP)    ................................. 05014074

(51) Int. Cl.
*G02B 1/06*    (2006.01)

(52) U.S. Cl. .................................................... 359/666

(58) Field of Classification Search .................. 359/666; 623/6.13, 6.22
See application file for complete search history.

(56) References Cited

U.S. PATENT DOCUMENTS

| | | | |
|---|---|---|---|
| 6,369,954 B1 | 4/2002 | Berge et al. | |
| 6,538,823 B2 | 3/2003 | Kroupenkine et al. | |
| 2002/0085172 A1 | 7/2002 | Altmann | |
| 2004/0227063 A1 | 11/2004 | Viinikanoja | |
| 2005/0002113 A1 | 1/2005 | Berge | |
| 2006/0170864 A1* | 8/2006 | Kuiper et al. | ................ 351/205 |

FOREIGN PATENT DOCUMENTS

| | | |
|---|---|---|
| DE | 19623270 A1 | 1/1998 |
| JP | 1140118 A1 | 6/1989 |
| WO | 9918456 A1 | 4/1999 |
| WO | 2004049927 A1 | 6/2004 |
| WO | WO 2004/088613 | 10/2004 |
| WO | 2005088910 A2 | 9/2005 |
| WO | WO2005/088610 A2 | 9/2005 |

OTHER PUBLICATIONS

International Search Report (PCT/EP2006/006028).

* cited by examiner

*Primary Examiner*—Joseph Martinez
(74) *Attorney, Agent, or Firm*—Haynes and Boone LLP

(57) ABSTRACT

A liquid lens system comprises a liquid drop 10 whose shape can be influenced by electrical fields. A plurality of electrodes are arranged annularly around the liquid drop. The liquid lens system may be employed in an artificial eye, an accommodation measuring instrument and a dioptric telescope.

8 Claims, 4 Drawing Sheets

ARTIFICIAL EYE AND MEASURING INSTRUMENT FOR MEASURING THE ACCOMMODATION OF AN EYE

CROSS REFERENCE

This application was originally filed as Patent Cooperation Treaty Application Number PCT/EP2006/006028 filed Jun. 22, 2006, which claims priority of European Application Number 05014074.8, filed Jun. 29, 2005.

CROSS-REFERENCE TO RELATED APPLICATION

This application is a United States national phase application of co-pending international patent application number PCT/EP2006/006028, filed Jun. 22, 2006, the disclosure of which is incorporated herein by reference.

BACKGROUND

The invention relates to an artificial eye and to a measuring instrument for measuring the accommodation of an eye, having a liquid lens system.

The prior art (products from Varioptic and Philips; U.S. Pat. No. 6,369,954 and EP 1 019 758) discloses controllable liquid lenses, with which the refractive power can be controlled in the range of about −15 dpt to 30 dpt within time intervals of a few milliseconds with voltages of up to 100 V.

JP 011 40 118 describes a lens whose surface is formed by a resilient wall, which can be deformed by modification of electrical voltages.

SUMMARY

It is an object of the invention to provide an artificial eye with which comprehensive and informative measurements can be carried out for the purpose of comparison with measurement on eyes in vivo.

To this end the invention provides an artificial eye having the features of patent claim 1. Advantageous configurations of the artificial eye are described in the claims dependent on claim 1.

Another configuration of the artificial eye provides an adjustable pupil in the beam path between the said lenses.

According to another configuration, in order to improve the measurement results and in particular to obtain reproducible measurement results under varying conditions, the artificial eye is equipped with a laser beam source for generating a beam comprising a multiplicity of parallel light rays, a CCD camera for recording images generated by the light rays after they pass through the lenses, and with a computer for processing the images and for controlling the liquid lens system as a function of the image processing.

The invention furthermore provides a measuring instrument for measuring the accommodation of an eye, having a liquid lens system which comprises two liquid lenses with the features of claim 4.

A preferred configuration of this measuring instrument provides a display screen for representing an image, which is formed on the retina of the eye. Another configuration of the measuring instrument provides a computer for controlling the representation of the image so that the image size and/or the brightness of the image represented on the display screen is/are adapted so that the brightness and size of the image on the retina is independent of the visual defect to be examined. For a patient who sees sharply at a longer distance, for example, a point must be adjusted more brightly than for a patient who sees sharply in the near field.

Lastly, another configuration of the measuring instrument provides two liquid lens systems and a computer, which drives one liquid lens system for a spherical correction whereas it drives the other liquid lens system for a cylinder correction.

A liquid lens system of the type mentioned above may furthermore be used advantageously in a dioptric telescope. Such a dioptric telescope contains preferably a liquid lens system for adjusting a refractive power and preferably a liquid lens system for adjusting a cylinder.

BRIEF DESCRIPTION OF THE DRAWINGS

Exemplary embodiments will be explained in more detail below with the aid of the drawing, in which.

DETAILED DESCRIPTION

Figure 1:
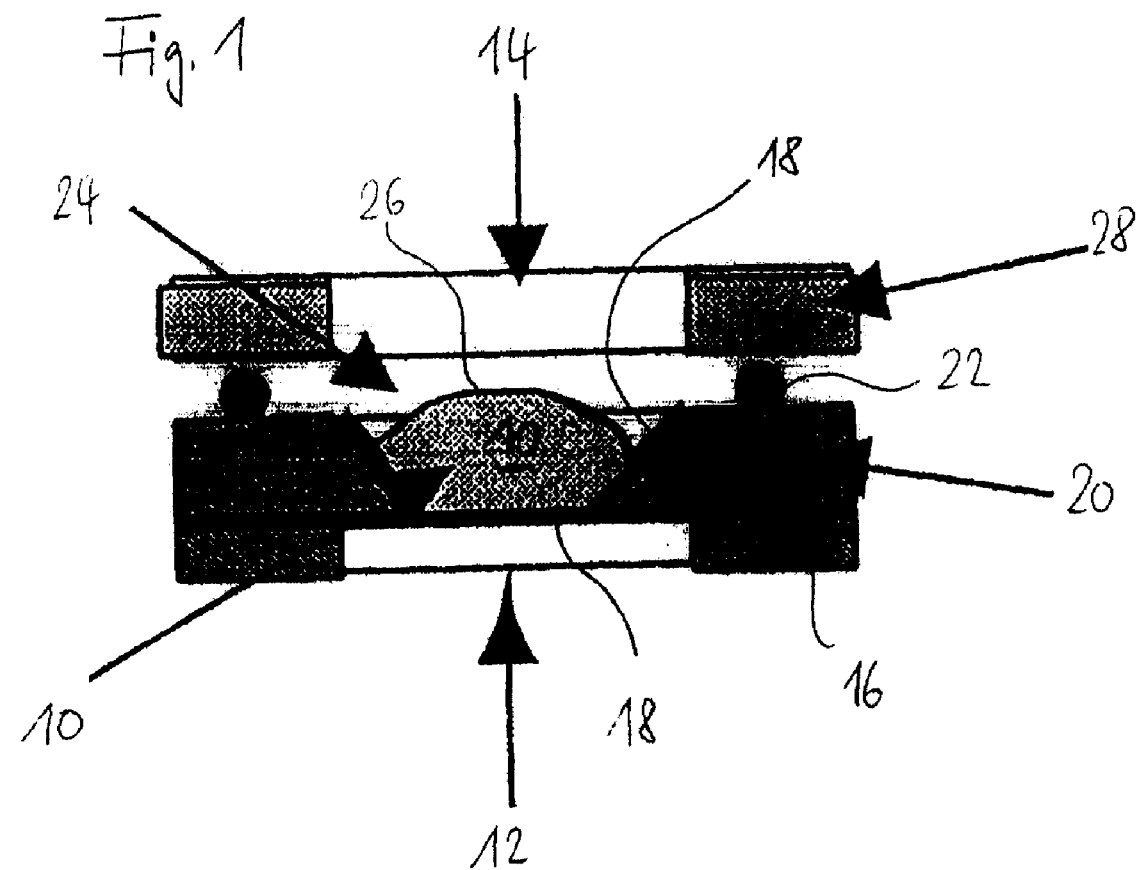
FIG. 1 schematically shows a section through a liquid lens system.

According to FIG. 1 a liquid drop 10, in the exemplary embodiment represented an oil drop, is arranged between two radiation-transparent windows 12, 14. Radiation (light) to be imaged is refracted by the liquid drop 10 in an adjustable way.

The liquid drop 10 rests on a transparent interlayer 18, which is in turn supported by a support ring 16.

Figure 2:
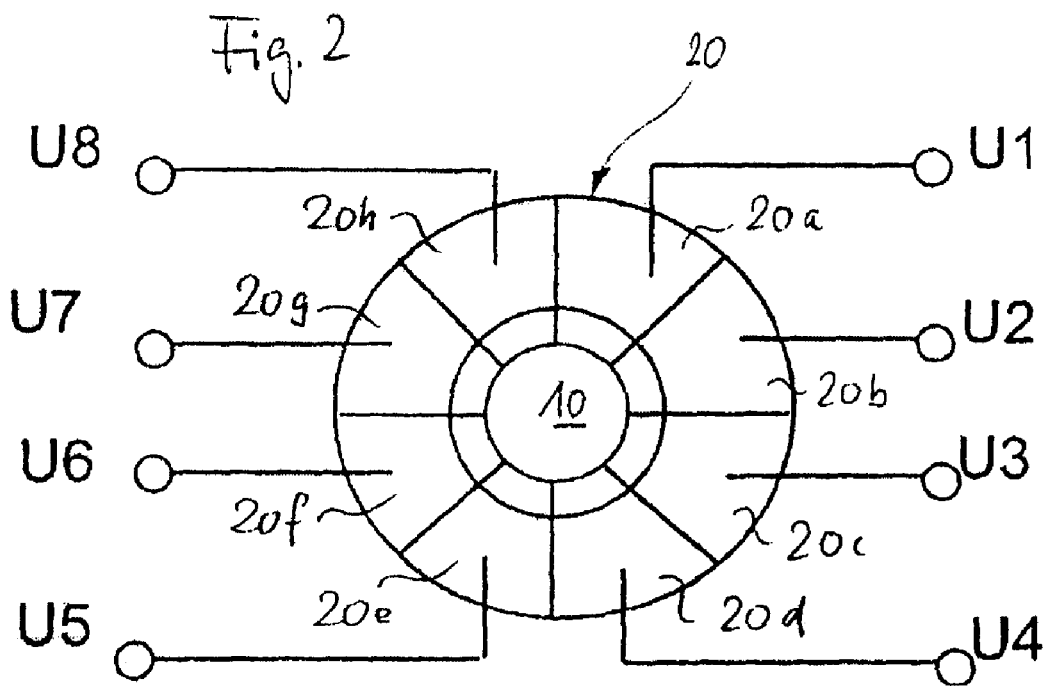
FIG. 2 schematically shows a plan view of the electrode arrangement of a liquid lens system according to FIG. 1.

An electrode ring 20, which is represented in a plan view in FIG. 2, is arranged around the liquid drop 10. As shown by FIG. 2, the electrode ring 20 in the exemplary embodiment represented consists of eight segments (20a, 20b, 20c, 20d, 20e, 20f, 20g, 20h). The said segments form a closed circle. FIG. 2 also shows the electrical voltages U1, U2, U3, U4, U5, U6, U7 and U8 which can selectively be applied respectively to the individual segments. By applying different voltages to the individual segments, the surface 26 of the liquid drop 10 can be modified so that the refractive properties of the liquid drop 10 are selectively adjustable. A ring 28 forms an e.g. "earthed" back electrode for the individual electrodes 20a, . . . , 20h. In order to replicate a cylinder lens, for example, the voltages U2, U3, U6, U7 must be set to a first voltage potential and the voltages U1, U4, U5, U8 of the other segments must be set to a different voltage potential. In this way, a lens defect can be set up electrically with a liquid lens system according to FIGS. 1 and 2, for example a sphere, a cylinder, coma or other defects of higher order. The more segments there are arranged around the liquid drop 10 similarly as in FIG. 2, the higher is the spatial resolution of the lens defects which can be adjusted. The arrangement of the individual electrode segments (20a, . . . , 20h) need not necessarily be rotationally symmetric. The exemplary embodiment according to FIG. 2 actually shows an eight-fold rotational symmetry of the electrodes, so that two electrodes in each case lie diametrically in relation to the liquid drop 10. As a variant of this exemplary embodiment, particularly in order to generate aspherical deformations of the liquid drop 10, the electrodes may be arranged differently from the representation according to FIG. 2 so that for the correction of typical imaging errors of the eye, deformations which are asymmetric in relation to the optical axis can be achieved and deformations can also be achieved in a controlled way locally as a function of the patient's visual defect. A deliberate deformation of the interface 26 of the liquid lens 10 is thus achieved.

Various exemplary applications of liquid lens systems of the type described above will be presented below.

Figure 3:
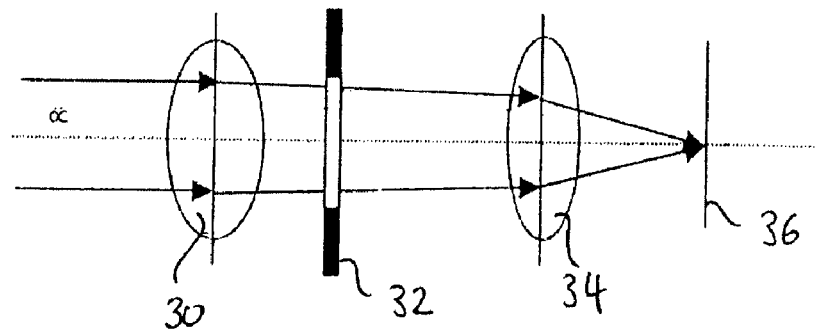
FIG. 3 shows an artificial eye.

FIG. 3 shows a so-called artificial eye, i.e. a device with the aid of which the visual defect of the human eye can be replicated for examination purposes etc. In FIG. 3, the radiation comes from the left. The first lens 30 is used to replicate the corneal curvature radius of the cornea of the eye. The radiation subsequently passes through a pupil 32 whose aperture is adjustable, for example electrically or mechanically. The radiation then passes through a liquid lens system 34 of the type described with the aid of FIGS. 1 and 2. The liquid lens system 34 thus makes it possible to adjust lens defects electrically by selectively applying different voltages U1, ..., U8. With the described optical system, the radiation is imaged onto an (artificial) retina 36, where it can be examined.

Figure 4:
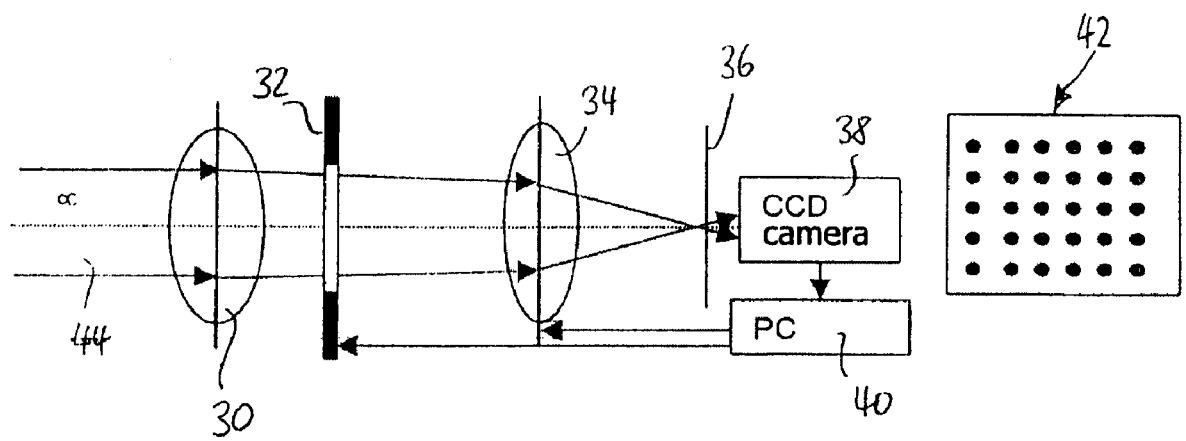
FIG. 4 shows a metrological layout of an artificial eye according to FIG. 3.

FIG. 4 shows a configuration of the artificial eye according to FIG. 3 such that it is possible to obtain reproducible measurement results, in which for example temperature-induced changes in the surface tension of the liquid drop are compensated for. It is thereby also possible to balance out control voltage fluctuations.

To this end, according to FIG. 4, a solid-state image camera 38 (for example a CCD camera) is arranged behind the (artificial) retina which is semitransparent for the radiation. The electrical image signals obtained by the camera are processed in a computer 40. By the computer 40, the pupil 32 and the liquid lens system 34 are driven in the manner indicated by arrows.

A beam 44 of parallel light rays, which are generated for example by a laser beam and a matricial diaphragm, enters the artificial eye parallel from the left according to FIG. 4. For example, one hundred parallel light rays may form the beam 44. The image generated by the light rays in the region of the retina 36 in the camera 38 is represented by the reference numeral 42 in FIG. 4 (only 30 rays, for the sake of simplicity).

The positions of the individual light rays, as they are imaged by the artificial eye, are measured by the camera 38. The lens defect can be determined accurately from the position of the individual laser arrays. The measurement result is used either in order to assess the lens defect or in order to determine a lens defect correction, by correcting deviations from the expected lens defect via the said control voltages U1 to U8. With the installed liquid lens system 34, the sphere and the cylinder of the artificial eye can be adjusted electrically.

The exemplary embodiment represented in FIGS. 3 and 4 may be expanded to the extent that a plurality of liquid lens systems of the described type are arranged successively staggered in the beam path, so that the measurement range and the adjustment accuracy are increased.

Figure 5:
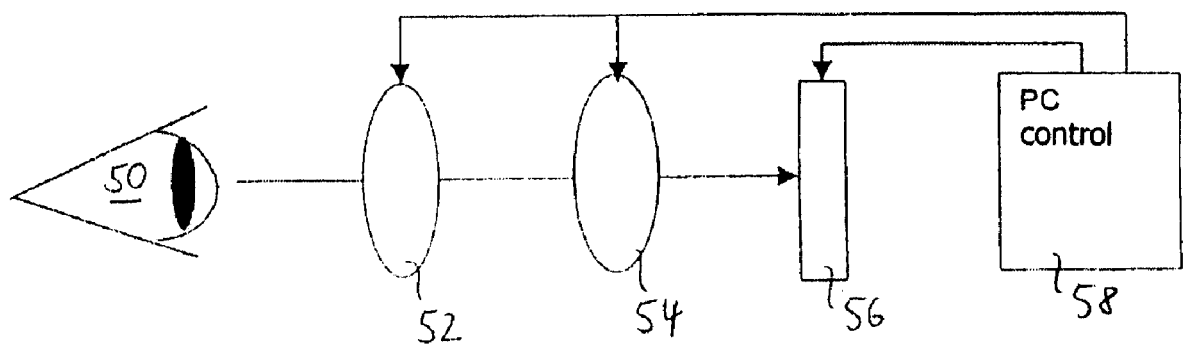
FIG. 5 shows an accommodation measuring instrument.

FIG. 5 shows an application of liquid lens systems according to FIGS. 1 and 2 in a so-called accommodation measuring instrument.

The measuring instrument according to FIG. 5 is constructed relatively simply and makes it possible to measure the accommodation capacity of a human eye with high accuracy.

An object is imaged onto the retina of the eye 50 to be examined as an image via two liquid lens systems 52, 54. The display screen 56 functions both as an object and as a target. A TFT display screen is preferably employed as the display screen 56, or alternatively for example a CRT display screen.

No mechanically moving parts need to be used for the measurement. A computer 58 controls the two liquid lens systems 52, 54 and the display screen 56. This arrangement particularly advantageously makes it possible for the brightness and the image size to be controlled with the display screen 56 so that the image formed contains the same brightness and size irrespective of the visual defect of the eye being examined. A more accurate measurement of the accommodation capacity is therefore possible. In order to measure the accommodation capacity, for example, a sphere may be modified in the microsecond range with the first liquid lens system 52 by applying suitable voltages U1, ..., U8 by means of the computer 58. The cylinder may be compensated for synchronously with the liquid lens system 54. The accommodation capacity of the eye 50 being examined can be determined by changing the frequency of the generated image modification and examining the image formed on the retina by means of the display screen 56.

By adding further liquid lens systems or normal lenses to the arrangement according to FIG. 5, it is possible to increase the measurement range as well as the measurement accuracy.

Figure 6:
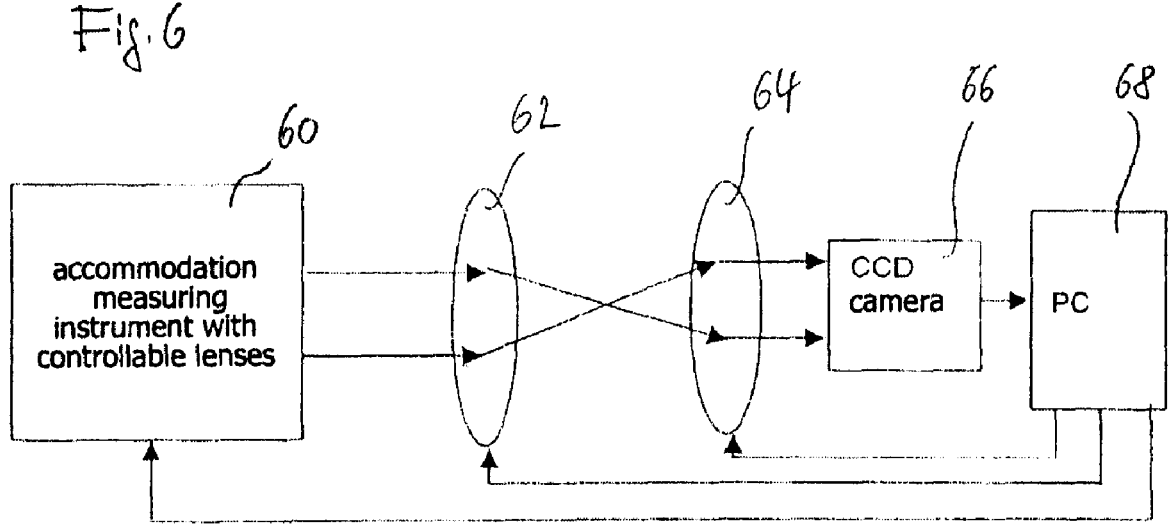
FIG. 6 shows a dioptric telescope.

FIG. 6 shows an arrangement which can be used as a dioptric telescope, i.e. a measuring instrument for determining the dioptric value of an eye to be examined. The block 60 in FIG. 6 is denoted as an accommodation measuring instrument with controllable lenses, i.e. the block 60 may represent a system as described above with the aid of FIG. 5. With the arrangement according to FIG. 6, for example, an accommodation measuring instrument 60 may be checked and calibrated.

According to FIG. 6, two liquid lens systems 62, 64 are arranged in the beam path after the accommodation measuring instrument. The radiation thereby generated is imaged into a CCD camera 66. The image signals of the camera 66 are processed in a computer 68. In the manner indicated by arrows, the computer 68 controls the accommodation measuring instrument, the solid-state lens system 62 and the solid-state lens system 64, i.e. in the latter cases the adjustable voltages U1, ..., U8 explained above.

With the said liquid lens systems, it is possible both to correct the refractive power and to compensate for the cylinder. Software in the computer 68 evaluates the digitally obtained image.

The arrangement according to FIG. 6 is small and compact. It is exclusively electrically controllable and allows straightforward calibration, so that the calibration also entails a time saving. Elaborate mechanics and optics can thus be obviated. The structure according to FIG. 6 also allows straightforward documentation of the calibration process by means of the computer, and it allows objective calibration.

In order to calibrate the accommodation measuring instrument 60, a defined refractive power (for example −3 dpt) is adjusted with the first liquid lens system 62 and a defined cylinder (for example 1 dpt 20°) is adjusted by means of the liquid lens system 64.

The refractive power and the cylinder are subsequently compensated for in the accommodation measuring instrument with the said controllable lenses. The camera 66 records an image and the computer 68 evaluates this image by means of image processing software. The image size must in this case correspond to the setpoint image size, otherwise the compensation in the accommodation measuring instrument must be continued until the image recorded by the camera 66 has reached the expected image size. The computer 68 also under-takes the control of the lenses in the accommodation measuring instrument 60.

An accommodation measuring instrument may furthermore be checked with the arrangement according to FIG. 6. To this end a defined refractive power (for example −3 dpt) and a defined cylinder (for example 1 dpt 20°) are adjusted in the accommodation measuring instrument. The dioptric telescope according to FIG. 6 is then adjusted to the same refractive power (for example −3 dpt) and the same cylinder (for example 1 dpt 20°). If the accommodation measuring instrument is correctly calibrated, then the image size of the image measured by the camera 66 must coincide with the setpoint image.

The dioptric telescope according to FIG. 6 may be extended in its measurement range by a combination of further liquid lens systems, optionally with glass or plastic lenses, and improved in respect of the measurement accuracy by precompensation.

What is claimed is:

1. Artificial eye, characterised by a liquid lens system having
   a liquid drop whose refractive property can be influenced by electrical fields;
   a plurality of electrodes which are arranged around the liquid drop;
   and an electrical voltage supply for selectively applying various voltages to the electrode in order to generate different electrical fields, and having
   a further lens, which replicates a corneal curvature.

2. Artificial eye according to claim 1, having an adjustable pupil between the lenses.

3. Artificial eye according to claim 2, having a laser beam source for generating a beam comprising a multiplicity of parallel light rays, a CCD camera for recording images generated by the light rays after they pass through the lenses, and having a computer for processing the images and for controlling the liquid lens system as a function of the image processing.

4. Artificial eye according to claim 1, having a laser beam source for generating a beam comprising a multiplicity of parallel light rays, a CCD camera for recording images generated by the light rays after they pass through the lenses, and having a computer for processing the images and for controlling the liquid lens system as a function of the image processing.

5. Measuring instrument for measuring the accommodation of the eye, having a liquid lens system which comprises two liquid lenses that are respectively provided with
   a liquid drop whose refractive property can be influenced by electrical fields;
   a plurality of electrodes which are arranged around the liquid drop;
   and an electrical voltage supply for selectively applying various voltages to the electrode in order to generate different electrical fields, and having
   a computer for synchronously applying voltages to the electrodes of the liquid lenses.

6. Measuring instrument according to claim 5, having a display screen for representing an image on the retina of the eye.

7. Measuring instrument according to claim 6, having a computer for controlling the representation of an image so that the image size and/or the brightness of the image on the display screen are independent of the visual defect of the eye.

8. Measuring instrument according to claim 5, wherein the computer drives one liquid lens system for a spherical correction and the other liquid lens system for a cylinder correction.

* * * * *